(12) United States Patent
Mishima

(10) Patent No.: US 10,330,652 B2
(45) Date of Patent: Jun. 25, 2019

(54) AUTOMATIC ANALYSIS METHOD, AUTOMATIC ANALYSIS APPARATUS, AND PROGRAM FOR THE AUTOMATIC ANALYSIS APPARATUS EACH USING MULTIVARIATE CURVE RESOLUTION

(71) Applicant: SHIMADZU CORPORATION, Kyoto-shi, Kyoto (JP)

(72) Inventor: Kenichi Mishima, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 438 days.

(21) Appl. No.: 14/422,794

(22) PCT Filed: Apr. 2, 2013

(86) PCT No.: PCT/JP2013/060099
§ 371 (c)(1),
(2) Date: Feb. 20, 2015

(87) PCT Pub. No.: WO2014/038234
PCT Pub. Date: Mar. 13, 2014

(65) Prior Publication Data
US 2015/0227491 A1 Aug. 13, 2015

(30) Foreign Application Priority Data
Sep. 7, 2012 (JP) ................. 2012-196962

(51) Int. Cl.
*G01N 30/86* (2006.01)
*G06F 17/10* (2006.01)
*G01N 21/27* (2006.01)

(52) U.S. Cl.
CPC .............. *G01N 30/86* (2013.01); *G01N 21/27* (2013.01); *G01N 30/8686* (2013.01);
(Continued)

(58) Field of Classification Search
CPC ........ G06F 17/10; G06F 19/10; G06F 19/703; G06F 19/705; G01N 30/86; G01N 30/8686; G01N 30/8696
See application file for complete search history.

(56) References Cited

U.S. PATENT DOCUMENTS 6,157,868 A * 12/2000 Abe .................. B26D 5/00
700/131
6,341,257 B1 * 1/2002 Haaland .................. G01J 3/28
702/22

(Continued)

FOREIGN PATENT DOCUMENTS

JP 2009-540322 A 11/2009
WO 2007/144664 A1 12/2007

OTHER PUBLICATIONS

Communication dated Apr. 8, 2016, from the European Patent Office in counterpart European application No. 13835939.3.
(Continued)

*Primary Examiner* — Michael Jung
(74) *Attorney, Agent, or Firm* — Sughrue Mion, PLLC

(57) ABSTRACT

Provided are an automatic analysis method, an automatic analysis apparatus, and a program for the automatic analysis apparatus capable of discriminating a number of components included in a sample more accurately and easily. Components are discriminated based on respective pieces of resolution spectral data obtained by multivariate curve resolution (MCR) using a provisional number of components k, and the number of components included in the sample is determined based on a discriminated result. At this time, the multivariate curve resolution is repeated (steps S103 to S108) until a border value between the provisional number of components k in a case where the components are discriminated as being different in all the pieces of the resolution spectral data obtained by the multivariate curve (Continued)

resolution and the provisional number of components k in a case where the components are discriminated as being matched in at least two pieces of the resolution spectral data in all the pieces of the resolution spectral data obtained by the multivariate curve resolution is obtained. As a result, the number of components included in the sample can be discriminated more accurately and easily based on the obtained border value (step S113).

9 Claims, 7 Drawing Sheets

(52) U.S. Cl.
CPC ......... *G01N 30/8696* (2013.01); *G06F 17/10* (2013.01); *G01N 2201/1293* (2013.01)

(56) References Cited

U.S. PATENT DOCUMENTS

| | | | |
|---|---|---|---|
| 6,584,413 B1* | 6/2003 | Keenan | G06K 9/6247 702/194 |
| 6,675,106 B1* | 1/2004 | Keenan | G01J 3/28 702/194 |
| 2007/0043518 A1* | 2/2007 | Nicholson | G06F 19/703 702/23 |
| 2007/0133984 A1* | 6/2007 | Maier | G01J 3/28 398/26 |
| 2007/0147685 A1* | 6/2007 | Ericson | G06K 9/6253 382/225 |
| 2007/0168154 A1* | 7/2007 | Ericson | G06K 9/6247 702/179 |
| 2009/0097020 A1* | 4/2009 | Treado | G01N 21/64 356/301 |
| 2010/0198524 A1* | 8/2010 | Brown | G01J 3/28 702/27 |
| 2012/0065948 A1* | 3/2012 | Tan | G01J 3/28 703/2 |
| 2013/0082180 A1* | 4/2013 | Priore | G01N 21/55 250/339.07 |
| 2013/0096847 A1* | 4/2013 | Yamaguchi | G01N 30/86 702/23 |
| 2013/0096883 A1* | 4/2013 | Bradley | G01N 21/35 702/189 |

OTHER PUBLICATIONS

Vivo-Truyols et al., "Towards unsupervised analysis of second-order chromatographic data: Automated selection of number of components in multivariate curve-resolution methods", Journal of Chromatography A, 2007, vol. 1158, pp. 258-272 (15 pages total).

Wasim et al., "Determination of the number of significant components in liquid chromatography nuclear magnetic resonance spectroscopy", Chemometrics and Intelligent Laboratory Systems, 2004, vol. 72., pp. 133-151 (19 pages total).

Garrido et al., "Multivariate curve resolution-alternating least squares (MCR-ALS) applied to spectroscopic data from monitoring chemical reactions processes", Anal Bioanal Chem, vol. 390, 2008, pp. 2059-2066 (8 pages total).

* cited by examiner

A

B

AUTOMATIC ANALYSIS METHOD, AUTOMATIC ANALYSIS APPARATUS, AND PROGRAM FOR THE AUTOMATIC ANALYSIS APPARATUS EACH USING MULTIVARIATE CURVE RESOLUTION

CROSS REFERENCE TO RELATED APPLICATIONS

This application is a National Stage of International Application No. PCT/JP2013/060099, filed on Apr. 2, 2013, which claims priority from Japanese Patent Application No. 2012-196962, filed on Sep. 7, 2012, the contents of all of which are incorporated herein by reference in their entirety.

TECHNICAL FIELD

The present invention relates to an automatic analysis method, an automatic analysis apparatus and a program for the automatic analysis apparatus for analyzing a component included in a sample by using multivariate curve resolution.

BACKGROUND ART

Conventionally, a component included in a sample is generally analyzed by using multivariate curve resolution (MCR) (for example, see Patent Documents 1 and 2). Resolution spectral data about respective components included in the sample is obtained by using the multivariate curve resolution, and the components can be discriminated based on each pieces of the resolution spectral data.

At the time of an analysis, for example, a spectrum is detected at a plurality of measurement points on a sample surface, and a measurement data matrix D is obtained based on the spectrum at each of the measurement points. The following relational expression (1) is established for this measurement data matrix D. A symbol C is a concentration matrix presenting concentration of the components at each of the measurement points, a symbol $S^T$ is a transposed matrix of a spectral matrix S where spectra of the components are arranged, and a symbol E is a matrix of noise components included in the measurement data matrix D.

$$D = CS^T + E \tag{1}$$

In the multivariate curve resolution, C and $S^T$ are calculated based on the measurement data matrix D so that a sum of squares of the E component in the expression (1) is minimum. Such a process can be executed by using a publicly-known algorithm such as an Alternative Least Square (ALS). The spectra of the respective columns of the spectral matrix S obtained by the calculated $S^T$ compose the resolution spectral data of the components obtained by the multivariate curve resolution.

In the multivariate curve resolution, a number of components to be resolved should be set in advance. When k-number of components is assumed to be included in a sample, a resolved result of a data matrix can be expressed as the following expression (2) by using a concentration matrix $C_k$ and a spectral matrix $S_k$ obtained by the multivariate curve resolution. A symbol $S_k^T$ is a transposed matrix of the spectral matrix $S_k$, a symbol $E_k$ is a residual matrix. At this time, when the assumed number of the components k is different from the number of existent components, spectra and concentration distribution of the components obtained by the concentration matrix $C_k$ and the spectral matrix $S_k$ are different from spectra and concentration distribution of the components existent in the sample. For this reason, in order to obtain an appropriate resolved result, the multivariate curve resolution should be carried out after the number of components existent in the sample is set.

$$D = C_k S_k^T + E_k \tag{2}$$

PRIOR ART DOCUMENTS

Patent Documents

PATENT DOCUMENT 1: Japanese Patent Application Laid-Open No, 2011-257288
PATENT DOCUMENT 2: Japanese Translation of PCT International Application No. 2009-540322

SUMMARY OF THE INVENTION

Problems to be Solved by the Invention

In the analysis method using the multivariate curve resolution, the number of components to be resolved should be set in advance. For this reason, when an unknown sample is analyzed, a number of components included in the sample should be estimated by any method.

For example, a method with which an analyst checks peaks of spectra so as to estimate a number of components included in a sample is considered. In such a method, however, the analyst has to have an advanced knowledge of spectrum analysis, and it is difficult to specify components whose peaks are very small.

Further, for example, it is considered that the number of components included in a sample is estimated by another various methods such as a method for performing principal component analysis on a detected result of spectra and determining a number of main components until a cumulative contribution ratio exceeds a predetermined threshold as the number of components, and a method using a Malinowski's empirical function IND. However, estimated values of the number of components obtained by the respective methods vary, and thus the results vary dependently on the adopted methods.

The present invention is devised from the above circumstances, and its object is to provide an automatic analysis method, an automatic analysis apparatus, and a program for the automatic analysis apparatus capable of discriminating a number of components included in a sample more accurately and easily.

Means for Solving the Problems

An automatic analysis method of the present invention includes: a multivariate curve resolution executing step of executing multivariate curve resolution using a provisional number of components as a number of components included in a sample so as to obtain resolution spectral data whose number of pieces is the same as a provisional number of components; a component discriminating step of discriminating components based on the respective pieces of resolution spectral data obtained by the multivariate curve resolution; and a component number determining step of determining a number of the components included in the sample based on the result of discriminating the components, wherein at the multivariate curve resolution executing step, the multivariate curve resolution is repeated until a border value between a provisional number of components in a case where components are discriminated as being different in all the pieces of the resolution spectral data obtained by the multivariate curve resolution and a provisional number of components in a case where the components are discriminated as being matched in at least two pieces of the resolution spectral data in all the pieces of the resolution spectral data obtained by the multivariate curve resolution is obtained, at the component number determining step, a number of the components included in the sample is determined based on the border value.

In such a constitution, components are discriminated based on resolution spectral data obtained by multivariate curve resolution using a provisional number of components, and the number of components included in a sample can be determined based on the discriminated result. At this time, the multivariate curve resolution is repeated until a border value between a provisional number of components discriminated as being different in all the resolution spectral data obtained by the multivariate curve resolution and a provisional number of components discriminated as being matched in at least two pieces of the resolution spectral data in the respective pieces of the resolution spectral data obtained by the multivariate curve resolution is obtained. As a result, the number of components included in the sample can be discriminated more accurately and easily based on the border value.

At the multivariate curve resolution executing step, when the components are discriminated as being different in all the pieces of the resolution spectral data obtained by the multivariate curve resolution, a provisional number of components may be increased one by one so that the multivariate curve resolution is repeated until the components are discriminated as being matched in at least two pieces of the resolution spectral data in all the pieces of the resolution spectral data obtained by the multivariate curve resolution. In this case, at the component number determining step, when the components are discriminated as being matched in at least two pieces of the resolution spectral data in all the pieces of the resolution spectral data obtained by the multivariate curve resolution, a provisional number of components at that time may be used as the border value, and a value obtained by subtracting one from the border value may be determined as the number of components included in the sample.

In such a constitution, when components are discriminated as being different in all pieces of the resolution spectral data obtained by the multivariate curve resolution, a provisional number of components is increased one by one and the multivariate curve resolution is repeated until the components are discriminated as being matched in at least two pieces of the resolution spectral data in all pieces of the resolution spectral data obtained by the multivariate curve resolution, so that a border value (the provisional number of components) is obtained. As a result, the number of components included in the sample can be discriminated more accurately and easily based on the border value.

At the multivariate curve resolution executing step, when the provisional number of components reaches the predetermined repetition determined value, execution of the multivariate curve resolution may be ended.

In such a constitution, since unexpected repetition of the multivariate curve resolution caused by a noise component can be prevented, an analysis time can be shortened.

At the component discriminating step, a library of spectral data about known components may be used, and all the pieces of the resolution spectral data obtained by the multivariate curve resolution may be compared with the spectral data in the library, so that the components are discriminated.

In such a constitution, when components are discriminated by using a library of spectral data of known components, the discrimination of the number of the components included in the sample and identification of the components included in the sample can be performed simultaneously, and thus the sample can be analyzed efficiently.

At the component discriminating step, all the pieces of the resolution spectral data obtained by the multivariate curve resolution may be compared with each other, and the components may be discriminated based on whether similarities of the resolution spectral data are a predetermined threshold or more.

In such a constitution, the components are discriminated based on whether similarity of the respective pieces of the resolution spectral data is a predetermined threshold or more, so that the number of components included in the sample can be discriminated for a short time.

The automatic analysis method may further includes: a concentration distribution display step of displaying concentration distribution of the components discriminated at the component discriminating step as a chemical image.

In such a constitution, concentration distribution of the components is displayed as a chemical image so that an analyzed result can be displayed in a comprehensible way.

An automatic analysis apparatus of the present invention includes: a multivariate curve resolution execution processor for executing multivariate curve resolution using a provisional number of components as a number of components included in a sample, and obtaining resolution spectral data whose number of pieces is the same as a provisional number of components; a component discrimination processor for discriminating components based on all the pieces of the resolution spectral data obtained by the multivariate curve resolution; and a component number determination processor for determining the number of components included in the sample based on the result of discriminating the components, wherein the multivariate curve resolution execution processor repeats the multivariate curve resolution until a border value between a provisional number of components in a case where the components are discriminated as being different in all the pieces of the resolution spectral data obtained by the multivariate curve resolution and a provisional number of components in a case where the components are discriminated as being matched in at least two pieces of the resolution spectral data in all the pieces of the resolution spectral data obtained by the multivariate curve resolution is obtained, the component number determination processor determines the number of components included in the sample based on the border value.

A program for an automatic analysis apparatus of the present invention is for making a computer function as: a multivariate curve resolution execution processor for executing multivariate curve resolution using a provisional number of components as a number of components included in a sample, and obtaining resolution spectral data whose number of pieces is the same as a provisional number of components; a component discrimination processor for discriminating components based on all the pieces of the resolution spectral data obtained by the multivariate curve resolution; and a component number determining processor for determining the number of components included in the sample based on the result of discriminating the components, wherein the multivariate curve resolution execution processor repeats the multivariate curve resolution until a border value between a provisional number of components in a case where the components are discriminated as being different in all the pieces of the resolution spectral data obtained by the multivariate curve resolution and a provisional number of components in a case where the components are discriminated as being matched in at least two pieces of the resolution spectral data in all the pieces of the resolution spectral data obtained by the multivariate curve resolution is obtained, the component number determination processor determines the number of components included in the sample based on the border value.

Effects of the Invention

According to the present invention, components are discriminated based on the respective pieces of the resolution spectral data obtained by the multivariate curve resolution using a provisional number of components, and the number of components included in a sample is determined based on the discriminated result, so that the number of components included in the sample can be discriminated more accurately and easily.

MODE FOR CARRYING OUT THE INVENTION

Figure 1:
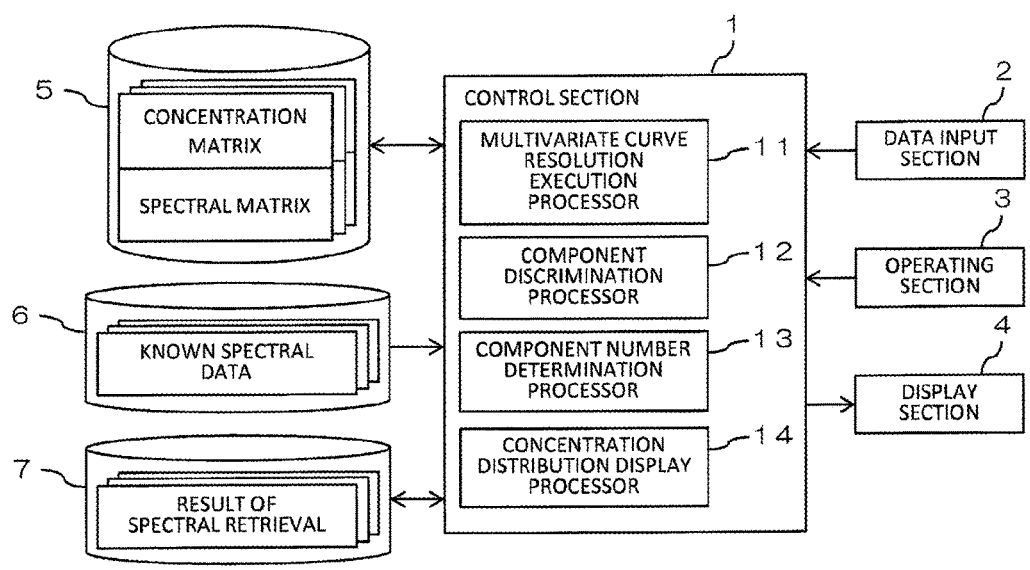
FIG. 1 is a block diagram illustrating a constitutional example of an automatic analysis apparatus according to one embodiment of the present invention.

FIG. 1 is a block diagram illustrating a constitutional example of an automatic analysis apparatus according to one embodiment of the present invention. The automatic analysis apparatus is an apparatus for analyzing components included in a sample by using multivariate curve resolution (MCR). The automatic analysis apparatus includes a control section 1, a data input section 2, an operating section 3, a display section 4, a multivariate curve resolution result storage section 5, a library storage section 6, and a spectral retrieval result storage section 7.

The control section 1 includes, for example, a CPU (Central Processing Unit), and executes programs so as to function as respective various function parts such as a multivariate curve resolution execution processor 11, a component discrimination processor 12, a component number determination processor 13, and a concentration distribution display processor 14. At the time of an analysis, a measuring device (not shown) detects spectra at a plurality of measurement points on a sample surface (a plurality of divided regions on the sample surface), for example, and a measurement data matrix D is obtained based on the spectra at the measurement points.

The measurement data matrix D can be obtained by, for example, transposing column vectors $d_1, d_2, \ldots, d_n$ representing spectra at n-number of measurement points and arranging them in tandem. The measurement data matrix D obtained in such a manner is input into the control section 1 via the data input section 2. The data input section 2 may be constituted so as to be connectable to the measuring device in a wired or wireless way, or so that data obtained by the measuring device is input into the data input section 2 via a storage medium. Further, the automatic analysis apparatus of the present invention can be constituted integrally with the measuring device.

The multivariate curve resolution result storage section 5, the library storage section 6, and the spectral retrieval result storage section 7 can be composed of one or a plurality of memories, namely, can be composed of, for example, a ROM (Read Only Memory) or a RAM (Random Access Memory). The operating section 3 includes, for example, a keyboard or a mouse, and an analyst operates the operating section 3 so as to be capable of performing input works. The display section 4 can be composed of, for example, a liquid crystal display, and thus analyzed results can be displayed on the display section 4.

The multivariate curve resolution execution processor 11 executes the multivariate curve resolution based on the measurement data matrix D input from the data input section 2. In order to perform the multivariate curve resolution, since the number of components to be resolved should be set in advance, the provisional number of components k is set as the number of components included in the sample in this embodiment, and the multivariate curve resolution is executed by using the provisional number of components k.

In the multivariate curve resolution, a concentration matrix $C_k$ and the spectral matrix $S_k$ in which a sum of squares of elements of a residual matrix $E_k$ in the following expression (3) is minimum are calculated based on the measurement data matrix D. Such a process can be executed by using, for example, a publicly known algorithm such as an alternating least squares method (ALS). A symbol $S_k^T$ in the following expression (3) is a transposed matrix of the spectral matrix $S_k$.

$$D = C_k S_k^T + E_k \quad (3)$$

The concentration matrix $C_k$ and the spectral matrix $S_k$ that are calculated (resolved) in the above manner are related with each other so as to be stored in the multivariate curve resolution result storage section 5. The spectra in the respective columns of the spectral matrix $S_k$ compose resolution spectral data about respective components obtained by the multivariate curve resolution, and the resolution spectral data whose number of pieces is the same as the provisional number of components k are obtained.

The component discrimination processor 12 discriminates components based on the respective pieces of resolution spectral data obtained by the multivariate curve resolution. In this embodiment, components can be discriminated by using a library of spectral data about known components (known spectral data) stored in the library storage section 6.

Concretely, the respective pieces of the resolution spectral data obtained by the multivariate curve resolution are compared with the respective pieces of known spectral data in the library stored in the library storage section 6, so that matched components are retrieved (spectral retrieval). This spectral retrieval can be performed in a manner that, for example, similarity between the respective pieces of the resolution spectral data and the respective pieces of known spectral data is calculated, and components corresponding to the known spectral data whose similarity is the highest are used as the retrieved result. As a result, components corresponding to the respective pieces of the resolution spectral data can be discriminated (identified), and the discriminated result (spectral retrieval result) is stored in the spectral retrieval result storage section 7.

In this embodiment, the provisional number of components k is set to "2" as an initial value so that the multivariate curve resolution is executed. When the components are discriminated as being different in all the pieces of the resolution spectral data obtained by the multivariate curve resolution, the provisional number of components k is increased one by one and the multivariate curve resolution is repeated until components are discriminated as being matched in at least two pieces of the resolution spectral data in all the pieces of the resolution spectral data obtained by the multivariate curve resolution.

That is to say, while components are discriminated as being different in all the pieces of the resolution spectral data obtained by the multivariate curve resolution, different components might be included in a sample. For this reason, the provisional number of components k is increased one by one and the multivariate curve resolution is executed. As a result of increasing the provisional number of components k one by one and repeating the multivariate curve resolution in such a manner, when components are discriminated as being matched in at least two pieces of the resolution spectral data in all the pieces of the resolution spectral data obtained by the multivariate curve resolution, the provisional number of components k can be discriminated as exceeding an actual number of components.

The provisional number of components k that is discriminated as exceeding the actual number of components is a border value between a provisional number of components (k−1) to be discriminated as different components in all the pieces of the resolution spectral data obtained by the multivariate curve resolution, and a provisional number of components (k) to be discriminated as the matched components in at least two pieces of the resolution spectral data in all the pieces of the resolution spectral data obtained by the multivariate curve resolution. In this embodiment, the multivariate curve resolution is repeated until the border value (the provisional number of components k) is obtained, and the number of components included in the sample can be determined based on the obtained border value.

The component number determination processor 13 determines the number of components included in the sample based on the result of the components discriminated by the component discrimination processor 12. In this embodiment, a value (k−1) obtained by subtracting one from the border value is determined as the number of components included in a sample based on the border value (the provisional number of components k) obtained in the above manner. That is to say, when the components are discriminated as being matched in at least two pieces of the resolution spectral data in all the pieces of the resolution spectral data obtained by the multivariate curve resolution, the provisional number of components k at this time is used as the border value, and a value obtained by subtracting one from the border value is determined as the number of components included in the sample.

The concentration distribution display processor 14 displays the concentration distribution of the components discriminated by the component discrimination processor 12 as a chemical image on the display section 4. Concretely, the concentration matrix $C_k$ obtained by the multivariate curve resolution is read from the multivariate curve resolution result storage section 5, and concentration of the respective components at the measurement points on the sample surface is displayed as image data on the display section 4. The concentration distribution of the components is displayed as the chemical image in such a manner so that the analyzed result can be displayed in a comprehensible way.

Figure 2:
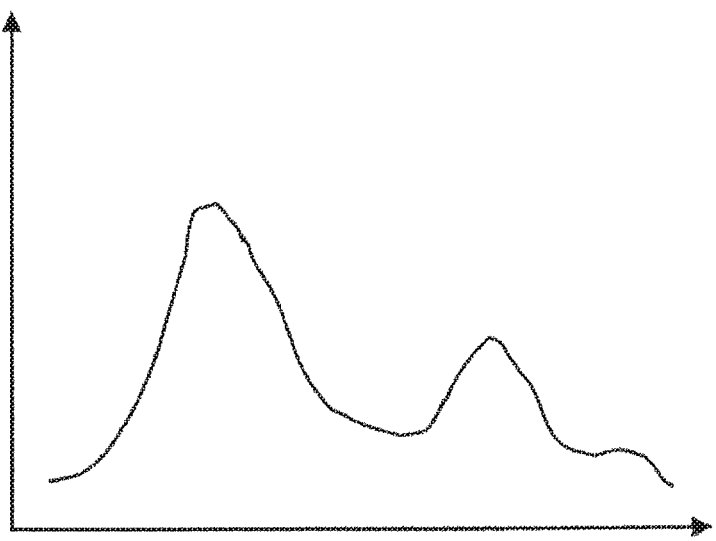
FIG. 2 is a diagram illustrating one example of the resolution spectral data in a case where the multivariate curve resolution is executed in a state that the provisional number of components k=2.
Figure 2:
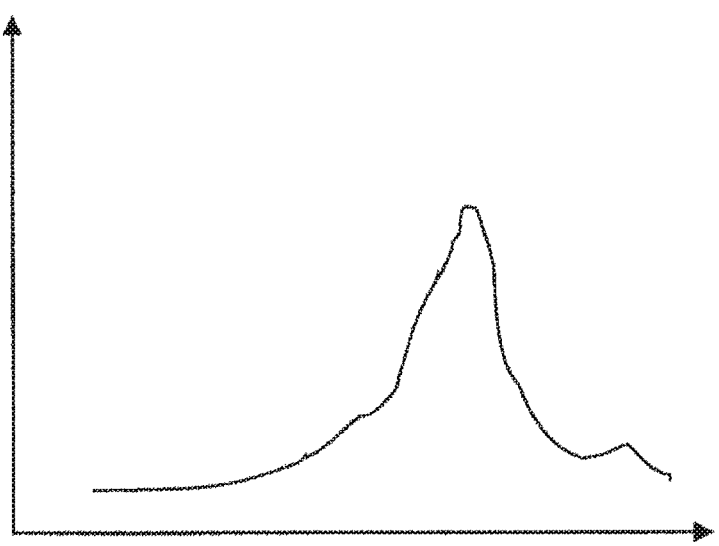

FIG. 2 is a diagram illustrating one example of the resolution spectral data in a case where the multivariate curve resolution is executed in a state that the provisional number of components k=2. In this example, two pieces of resolution spectral data obtained by the multivariate curve resolution are completely different from each other as shown in FIGS. 2A and 2B, and the components are discriminated as being different in two pieces of the resolution spectral data by the spectral retrieval in the component discrimination processor 12.

When the components are discriminated as being different in two pieces of the resolution spectral data obtained by the multivariate curve resolution, another components might be included in the sample. For this reason, the provisional number of components k is increased by one, and the multivariate curve resolution is again executed in a state that the provisional number of components k=3.

Figure 3:
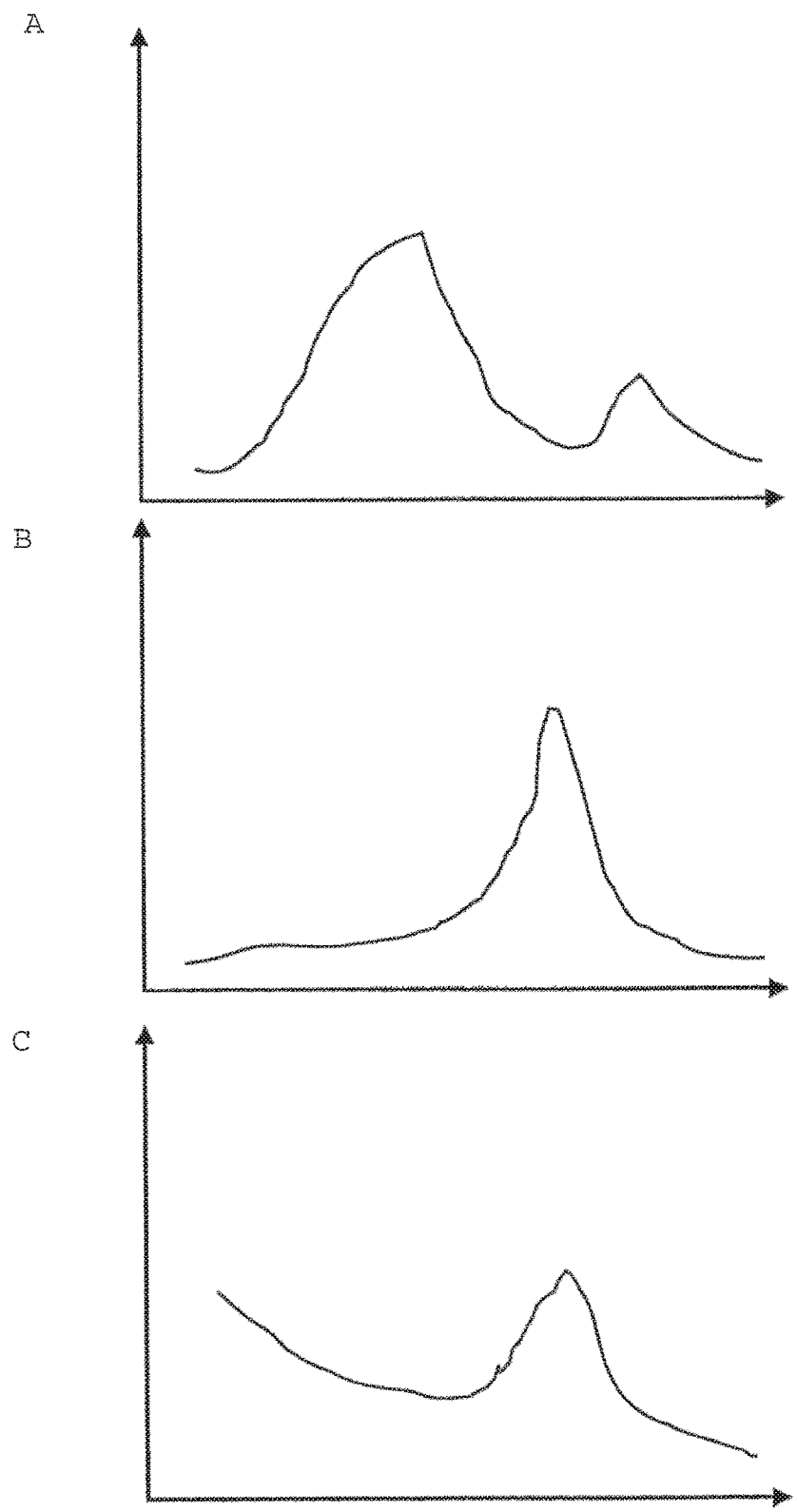
FIG. 3 is a diagram illustrating one example of the resolution spectral data in a case where the multivariate curve resolution is executed in a state that the provisional number of components k=3.

FIG. 3 is a diagram illustrating one example of the resolution spectral data in a case where the multivariate curve resolution is executed in a state that the provisional number of components k=3. In this example, three pieces of the resolution spectral data obtained by the multivariate curve resolution are as shown in FIGS. 3A, 3B and 3C, respectively, and the resolution spectral data is similar between FIGS. 3B and 3C.

When the components are discriminated as being matched in the two pieces of the resolution spectral data similar to each other by the spectral retrieval in the component discrimination processor 12, the provisional number of components k can be discriminated as exceeding the actual number of components. In this case, "2" that is a value obtained by subtracting one from the provisional number of components k is determined as the number of components included in the sample.

Figure 4:
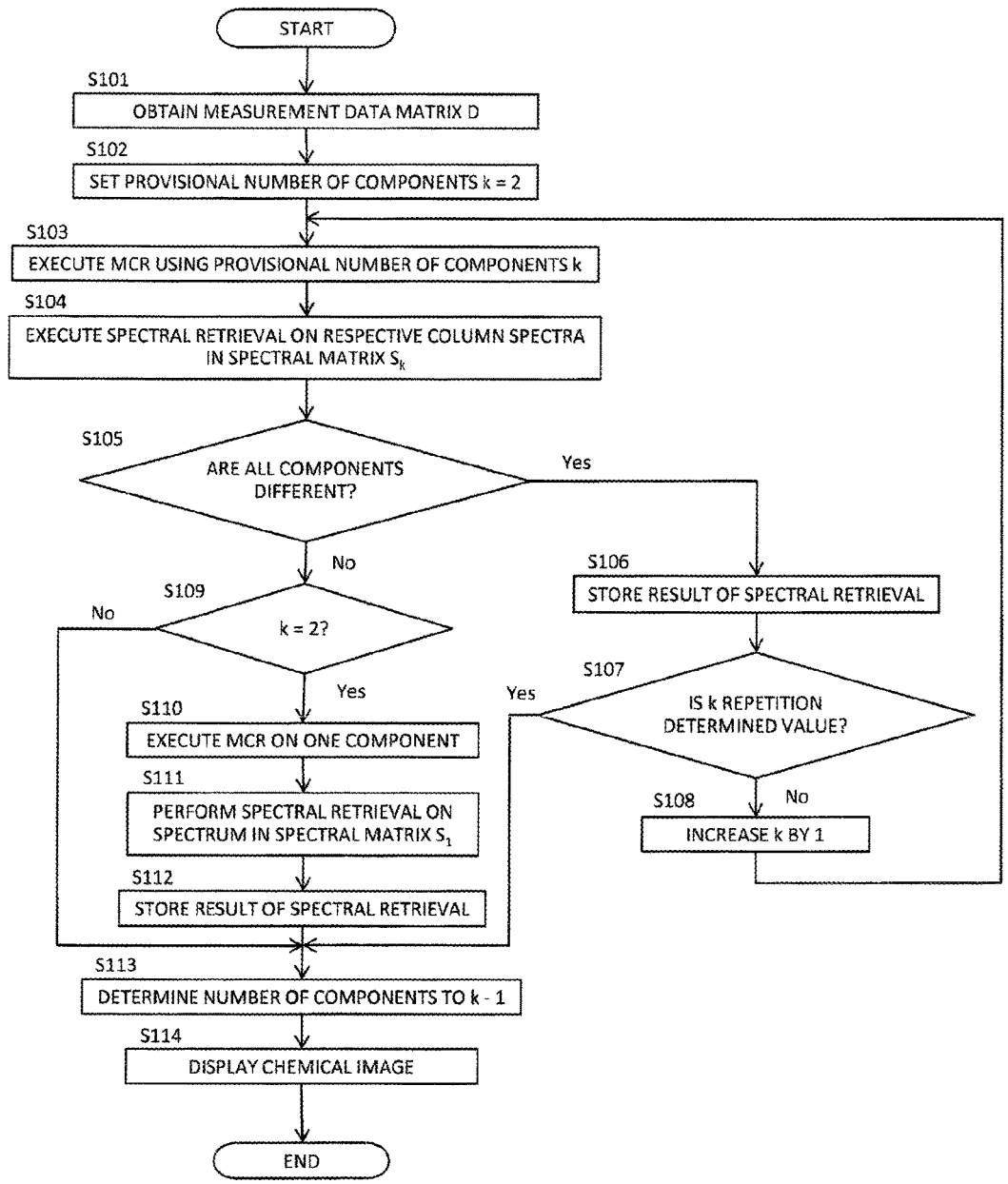
FIG. 4 is a flowchart illustrating one example of a process to be executed by the control section.

FIG. 4 is a flowchart illustrating one example of a process to be executed by the control section 1. At the time of an analysis, the measurement data matrix D is first obtained based on spectra detected at the plurality of measurement points on the sample surface (step S101). Thereafter, the provisional number of components k is set to "2" (step S102), and the multivariate curve resolution is executed by using the provisional number of components k (step S103: a multivariate curve resolution executing step).

As a result of the multivariate curve resolution, the concentration matrix $C_k$ and the spectral matrix $S_k$ are obtained so as to be stored in the multivariate curve resolution result storage section 5. Spectral retrieval is performed on the resolution spectral data of the respective components composing the spectra in the columns of the spectral matrix $S_k$ by using the known spectral data in the library stored in the library storage section 6 (step S104: a component discriminating step).

As a result of spectral retrieval, when the components are discriminated as being different in all the pieces of the resolution spectral data obtained by the multivariate curve resolution (Yes at step S105), the results of the spectral retrieval for the respective components are stored in the spectral retrieval result storage section 7 (step S106), and a determination is made whether the provisional number of components k at that time reaches a predetermined repetition determined value (step S107).

The repetition determined value can be set to any value that is 3 or more. The repetition determined value may be set as a defined value in advance, or the analyst operates the operating section 3 so as to be capable of setting the repetition determined value. Further, for example, the repetition determined value can be also set based on the number of components predicted from a cumulative contribution ratio by performing principal component analysis.

At a time point when the first multivariate curve resolution is executed, the provisional number of components k is "2" and thus does not reach the repetition determined value (No at step S107). For this reason, after the provisional number of components k is increased by one to "3" (step S108), the multivariate curve resolution is again executed (step S103: a multivariate curve resolution executing step). In this embodiment, the provisional number of components k is increased one by one so that the multivariate curve resolution is repeated until the components are discriminated as being matched in at least two pieces of the resolution spectral data in all the pieces of the resolution spectral data obtained by the multivariate curve resolution (until No at step S105).

During a process of repeating steps S103 to S108, when the provisional number of components k reaches the repetition determined value (Yes at step S107), the execution of the multivariate curve resolution is ended. In this case, the value (k−1) obtained by subtracting one from the provisional number of components k at that time is determined as the number of components included in the sample (step S113: a component number determining step), and the concentration distribution of the components is displayed as an analyzed result on the display section 4 in a form of a chemical image (step S114: a concentration distribution display step). When the provisional number of components k reaches the repetition determined value and the execution of the multivariate curve resolution is ended, this state may be displayed on the display section 4.

When the components are discriminated as being matched in at least two pieces of the resolution spectral data in all the pieces of the resolution spectral data obtained by the multivariate curve resolution with the provisional number of components k not reaching the repetition determined value (No at step S105), a determination is made whether the provisional number of components k at that time is "2" (step S109).

When the provisional number of components k is not "2" (No at step S109), the value (k−1) obtained by subtracting one from the provisional number of components k at that time is determined as the number of components included in the sample (step S113: the component number determining step). As the analyzed result, the concentration distribution of the components is displayed as a chemical image on the display section 4 (step S114: the concentration distribution display step).

On the other hand, when the provisional number of components k is "2" (Yes at step S109), namely, when the provisional number of components k is still an initial value, the multivariate curve resolution is performed with the number of components being "1" (step S110). A concentration matrix $C_1$ and a spectral matrix $S_1$ obtained as the result are stored in the multivariate curve resolution result storage section 5. Spectral retrieval is performed on the resolution spectral data of one component composing a spectrum in the spectral matrix $S_1$ by using respective pieces of known spectral data in the library stored in the library storage section 6 (step S111).

A result of the spectral retrieval is stored in the spectral retrieval result storage section 7 (step S112). At this time, since the provisional number of components k is "2", "1" obtained by subtracting one from the provisional number of components k is determined as the number of components included in the sample (step S113: the component number determining step). As the analyzed result, the concentration distribution of the component is displayed as a chemical image on the display section 4 (step S114: the concentration distribution display step).

The present invention is not limited to the constitution where the concentration distribution (chemical image) of the components is displayed on the display section 4 during a series of process including the multivariate curve resolution, and thus may have a constitution where the concentration distribution of the components may be displayed on the display section 4 in response to the operation of the operating section 3 performed by the analyst.

In this embodiment, components are discriminated based on the respective pieces of the resolution spectral data obtained by the multivariate curve resolution using the provisional number of components k, and the number of components included in the sample can be determined based on the discriminated result. At this time, the multivariate curve resolution is repeated until a border value between a provisional number of components discriminated as being different in all the pieces of the resolution spectral data obtained by the multivariate curve resolution and a provisional number of components discriminated as being matched in at least two pieces of the resolution spectral data in the respective pieces of the resolution spectral data obtained by the multivariate curve resolution is obtained. As a result, the number of components included in the sample can be discriminated more accurately and easily based on the border value.

Particularly, in this embodiment, when the components are discriminated as being different in all the pieces of the resolution spectral data obtained by the multivariate curve resolution, the number of components included in the sample can be discriminated more accurately and easily based on the border value (the provisional number of components k) that is obtained by increasing the provisional number of components k one by one and repeating the multivariate curve resolution until the components are discriminated as being matched in at least two pieces of the resolution spectral data in all the pieces of the resolution spectral data obtained by the multivariate curve resolution.

Further, in this embodiment, when the provisional number of components k reaches the predetermined repetition determined value, the execution of the multivariate curve resolution is ended. As a result, since unexpected repetition of the multivariate curve resolution caused by a noise component can be prevented, the analysis time can be shortened.

Further, components are discriminated by using the library of the spectral data of the known components (known spectral data), so that the discrimination of the number of components included in the sample and the identification of the components included in the sample can be made simultaneously, and thus the sample can be analyzed efficiently.

Figure 5:
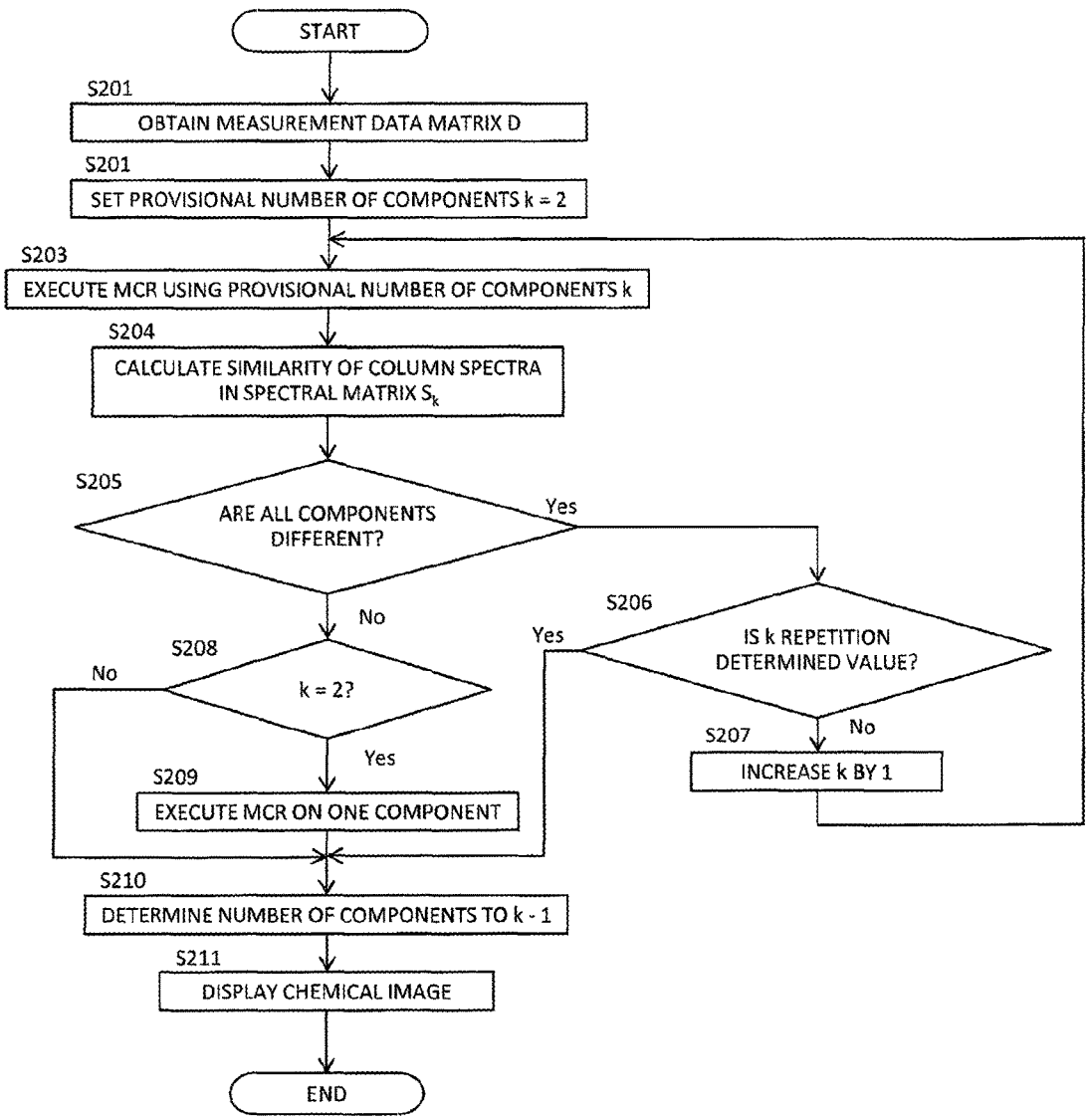
FIG. 5 is a flowchart illustrating one example of a process to be executed by the control section of the automatic analysis apparatus according to another embodiment.

FIG. 5 is a flowchart illustrating one example of a process to be executed by the control section 1 of the automatic analysis apparatus according to another embodiment. This embodiment is different from the above embodiment in that the components included in the sample are not discriminated (identified) by the spectral retrieval using the library of the known spectral data but are discriminated (distinguished) by comparing all the pieces of the resolution spectral data obtained by the multivariate curve resolution.

At the time of an analysis, the measurement data matrix D is first obtained based on spectra detected at a plurality of measurement points on a sample surface (step S201). Thereafter, the provisional number of components k is set to "2" (step S202), and the multivariate curve resolution is executed by using the provisional number of components k (step S203: the multivariate curve resolution executing step).

As a result of the multivariate curve resolution, the concentration matrix $C_k$ and the spectral matrix $S_k$ are obtained so as to be stored in the multivariate curve resolution result storage section 5. Similarity of the resolution spectral data of the respective components composing the spectra in the columns in the spectral matrix $S_k$ is calculated, so that the components are discriminated (step S204: a component discriminating step).

Concretely, the components are discriminated based on whether the similarity of the respective pieces of the resolution spectral data is a predetermined threshold or more. That is to say, when the similarity of the respective pieces of the resolution spectral data is the predetermined threshold or more, the components can be discriminated as being matched. When the similarity of the respective pieces of the resolution spectral data is less than the predetermined threshold, the components can be discriminated as being different from each other.

As a result, when the components are discriminated as being different in all the pieces of the resolution spectral data obtained by the multivariate curve resolution (Yes at step S205), the determination is made whether the provisional number of components k at that time reaches the predetermined repetition determined value (step S206).

The repetition determined value can be set to any value that is 3 or more. The repetition determined value may be set as a defined value in advance, or the analyst operates the operating section 3 so as to be capable of setting the repetition determined value. Further, for example, the repetition determined value can be also set based on the number of components predicted from a cumulative contribution ratio by performing principal component analysis.

At a time point when the first multivariate curve resolution is executed, the provisional number of components k is "2" and thus does not reach the repetition determined value (No at step S206). For this reason, after the provisional number of components k is increased by one into "3" (step S207), the multivariate curve resolution is again executed (step S203: the multivariate curve resolution executing step). In this embodiment, the provisional number of components k is increased one by one so that the multivariate curve resolution is repeated until the components are discriminated as being matched in at least two pieces of the resolution spectral data in all the pieces of the resolution spectral data obtained by the multivariate curve resolution (until No at step S205).

During the process for repeating steps S203 to S207, when the provisional number of components k reaches the repetition determined value (Yes at step S206), the execution of the multivariate curve resolution is ended. In this case, the value (k−1) obtained by subtracting one from the provisional number of components k at that time is determined as the number of components included in the sample (step S210: the component number determining step), and the concentration distribution of the components is displayed as a chemical image on the display section 4 (step S211: the concentration distribution display step). When the provisional number of components k reaches the repetition determined value and the execution of the multivariate curve resolution is ended, this state may be displayed on the display section 4.

When the components are discriminated as being matched in at least two pieces of the resolution spectral data in all the pieces of the resolution spectral data obtained by the multivariate curve resolution with the provisional number of components k not reaching the repetition determined value (No at step S205), the determination is made whether the provisional number of components k at that time is "2" (step S208).

When the provisional number of components k is not "2" (No at step S208), the value (k−1) obtained by subtracting one from the provisional number of components k at that time is determined as the number of components included in the sample (step S210: the component number determining step). As the analyzed result, the concentration distribution of the components is displayed as a chemical image on the display section 4 (step S211: the concentration distribution display step).

On the other hand, when the provisional number of components k is "2" (Yes at step S208), namely, the provisional number of components k is still an initial value, the multivariate curve resolution is executed with the number of components being "1" (step S209). At this time, since the provisional number of components k is "2", "1" obtained by subtracting one from the provisional number of components k is determined as the number of components included in the sample (step S210: the component number determining step). As the analyzed result, the concentration distribution of the component is displayed as a chemical image on the display section 4 (step S211: the concentration distribution display step).

The present invention is not limited to the constitution where the concentration distribution (chemical image) of the components is displayed on the display section 4 during a series of process including the multivariate curve resolution, and thus may have a constitution where the concentration distribution of the components may be displayed on the display section 4 in response to the operation of the operating section 3 performed by the analyst. Further, the components included in the sample may be additionally identified based on the spectral matrix $S_k$ obtained by the multivariate curve resolution.

In this embodiment, the components are discriminated based on whether the similarity of the respective pieces of the resolution spectral data is the predetermined threshold or more, so that the number of components included in the sample can be discriminated for a short time.

An embodiment where the number of components is discriminated by spectral retrieval using a sample in which two components including lactose and folic acid are mixed is described below. In this embodiment, the numbers of measurement points on a sample surface are 441 (21 rows× 21 columns).

Figure 6:
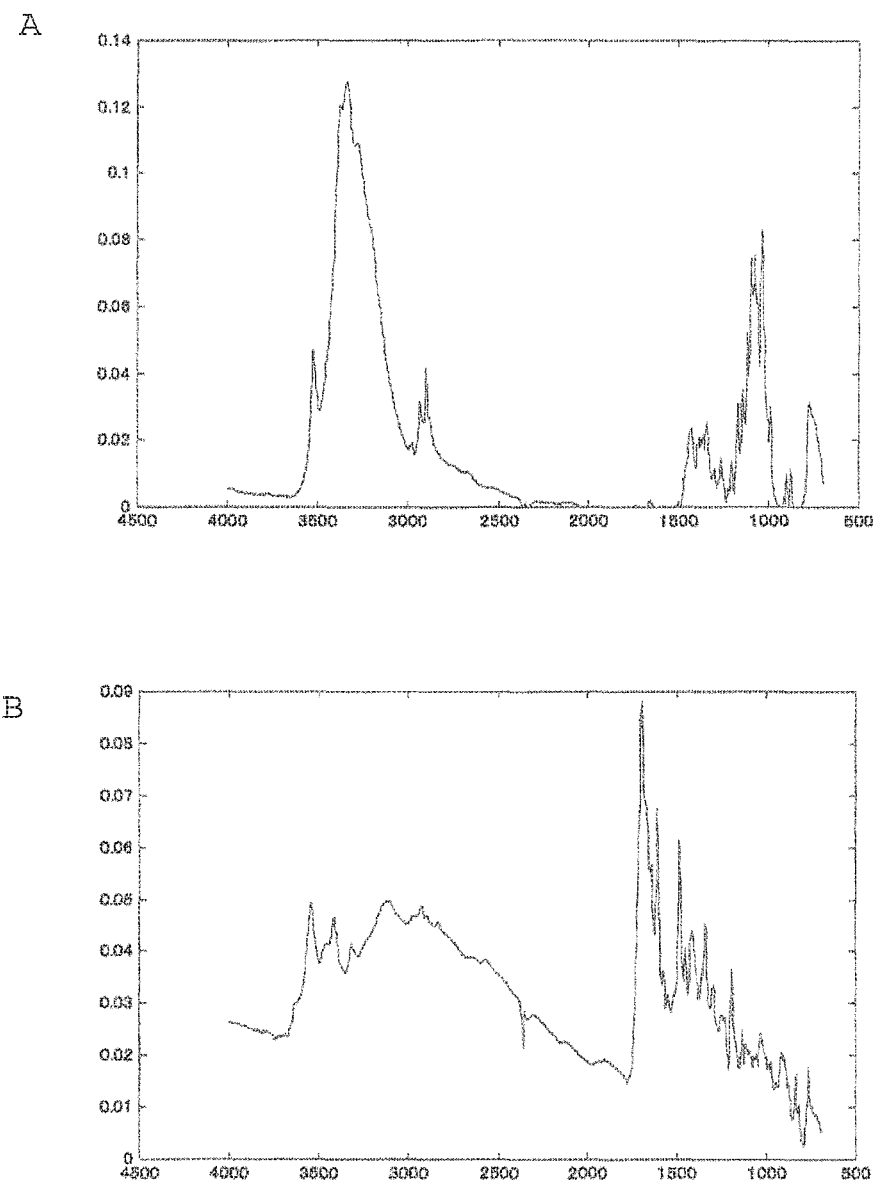
FIG. 6 is a diagram illustrating the resolution spectral data in a case where the multivariate curve resolution is executed in a state that the provisional number of components k=2 in the embodiment of the present invention.

FIG. 6 is a diagram illustrating the resolution spectral data in a case where the multivariate curve resolution is executed in a state that the provisional number of components k=2 in the embodiment of the present invention. As a result of the spectral retrieval, the discrimination is made as lactose in resolution spectral data in FIG. 6A. On the other hand, the discrimination is made as folic acid in the resolution spectral data in FIG. 6B as the result of the spectral retrieval.

When the components are discriminated as being different in two pieces of resolution spectral data obtained by the multivariate curve resolution, another components might be included in the sample. For this reason, the provisional number of components k is increased by one, and the multivariate curve resolution is again executed in a state that the provisional number of components k=3.

Figure 7:
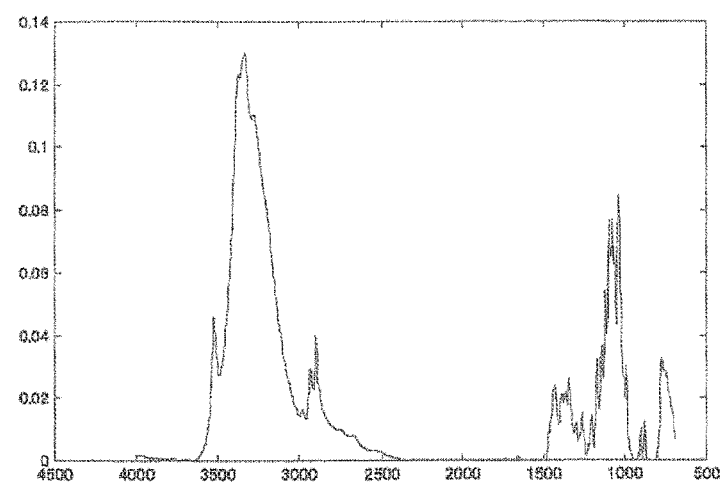
FIG. 7 is a diagram illustrating the resolution spectral data in a case where the multivariate curve resolution is executed in a state that the provisional number of components k=3 in the embodiment of the present invention.
Figure 7:
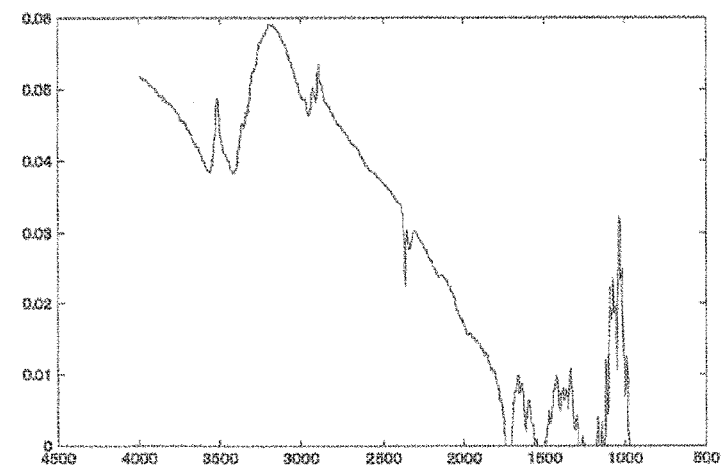
Figure 7:
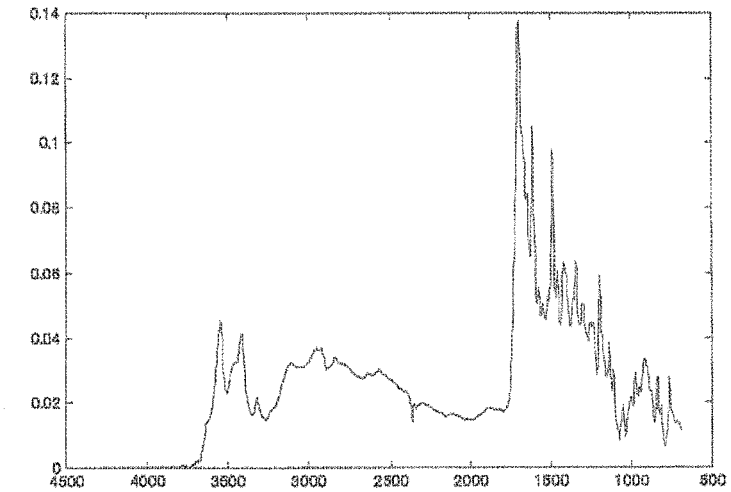

FIG. 7 is a diagram illustrating the resolution spectral data in a case where the multivariate curve resolution is executed in a state that the provisional number of components k=3 in the embodiment of the present invention. The components are discriminated as lactose as a result of the spectral retrieval in both the resolution spectral data in FIGS. 7A and 7B. On the other hand, the components are discriminated as folic acid as a result of the spectral retrieval in the resolution spectral data in FIG. 7C.

When the resolution spectral data in which the components are discriminated as being matched (lactose) through spectral retrieval is present, the provisional number of components k can be discriminated as exceeding the actual number of components. In this case, "2" that is obtained by subtracting 1 from the provisional number of components k is determined as the number of components included in the sample. This value is matched with the actual number of components included in the sample, and it is confirmed that the number of components included in the sample can be discriminated accurately.

This embodiment has described the constitution where the initial value of the provisional number of components k is set to "2" so that the multivariate curve resolution is executed. However, the initial value of the provisional number of components k is not limited to "2", and can be set to any value. In this case, the constitution may be such that the analyst can set the initial value of the provisional number of components k to any value.

Further, the present invention is not limited to the constitution where the provisional number of components k is increased one by one and the multivariate curve resolution is repeated, and the present invention may have, for example, a constitution where the provisional number of components k is decreased one by one and the multivariate curve resolution is repeated. That is to say, any other modes can be employed as a concrete mode as long as the multivariate curve resolution is repeated until the border value between the provisional number of components k in a case where the components are discriminated as being different in all the pieces of the resolution spectral data obtained by the multivariate curve resolution and the provisional number of components k in a case where the components are discriminated as being matched in at least two pieces of the resolution spectral data in all the pieces of the resolution spectral data obtained by the multivariate curve resolution is obtained.

Further, a program for making a computer to operate (the program for the automatic analysis apparatus) as the above-described automatic analysis device can be provided. In this case, the program may be structured so as to be provided in a form of a storage medium including the program, or the program itself may be provided.

DESCRIPTION OF REFERENCE SIGNS

1 control section
2 data input section
3 operating section
4 display section
5 multivariate curve resolution result storage section
6 library storage section
7 spectral retrieval result storage section
11 multivariate curve resolution execution processor
12 component discrimination processor
13 component number determination processor
14 concentration distribution display processor

The invention claimed is:

1. An automatic analysis apparatus for discriminating and determining the number of components included in a sample, said automatic analysis apparatus comprising:
   a measuring device which obtains a spectral data on components included in the sample,
   a data input section into which the spectral data is input from the measuring device,
   a multivariate curve resolution execution processor implemented by a CPU of the automatic analysis apparatus which executes instructions which sets a provisional number of components as a number of components included in the sample, and executes a multivariate curve resolution on the spectral data input into the data input section using the provisional number of components, and obtains resolution spectral data whose number of pieces is the same as a provisional number of components;
   a component discrimination processor implemented by the CPU which executes instructions which discriminates components based on all the pieces of the resolution spectral data obtained by the multivariate curve resolution;
   a component number determination processor implemented by the CPU which executes instructions which determines the number of components included in the sample based on the result of discriminating the components,
   wherein the multivariate curve resolution execution processor executes instructions which increases or decreases a provisional number of components, and repeats the multivariate curve resolution until a border value between a provisional number of components in a case where the components are discriminated as being different in all the pieces of the resolution spectral data obtained by the multivariate curve resolution and a provisional number of components in a case where the components are discriminated as being matched in at least two pieces of the resolution spectral data in all the pieces of the resolution spectral data obtained by the multivariate curve resolution is obtained,
   the component number determination processor determines the number of components included in the sample based on the border value, and
   the measuring device detects spectra at a plurality of measurement points on a surface of the sample, and obtains a measurement data matrix based on the spectra at each of the measurement points.

2. A non-transitory computer readable medium including a program product for an automatic analysis apparatus for discriminating and determining the number of components included in a sample for making an automatic analysis apparatus function as:
   a measuring device for obtaining spectral data on components included in the sample,
   a data input section into which the spectral data is input from the measuring device,
   a multivariate curve resolution execution processor implemented by a CPU of the automatic analysis apparatus for setting a provisional number of components as a number of components included in the sample, and executing a multivariate curve resolution on the spectral data input into the data input section using the provisional number of components, and obtaining resolution spectral data whose number of pieces is the same as a provisional number of components;

a component discrimination processor implemented by the CPU for discriminating components based on all the pieces of the resolution spectral data obtained by the multivariate curve resolution;

a component number determining processor implemented by the CPU for determining the number of components included in the sample based on the result of discriminating the components, wherein the multivariate curve resolution execution processor increases or decreases a provisional number of components, and repeats the multivariate curve resolution until a border value between a provisional number of components in a case where the components are discriminated as being different in all the pieces of the resolution spectral data obtained by the multivariate curve resolution and a provisional number of components in a case where the components are discriminated as being matched in at least two pieces of the resolution spectral data in all the pieces of the resolution spectral data obtained by the multivariate curve resolution is obtained, the component number determination processor determines the number of components included in the sample based on the border value, and the measuring device detects spectra at a plurality of measurement points on a surface of the sample, and obtains a measurement data matrix based on the spectra at each of the measurement points.

3. An automatic analysis method for discriminating and determining the number of components included in a sample, said automatic analysis method comprising:

a spectral data obtainment step executed by a measuring device, the spectral data obtainment step comprising obtaining a spectral data on components included in the sample, a data input step in which the spectral data is input into a data input section connectable to the measuring device, a multivariate curve resolution executing step executed by a multivariate curve execution processor implemented by a CPU of an automatic analysis apparatus, the multivariate curve resolution executing step comprising setting a provisional number of components as a number of components included in the sample, and executing a multivariate curve resolution on the spectral data input into the data input section using the provisional number of components so as to obtain resolution spectral data whose number of pieces is the same as a provisional number of components;

a component discriminating step executed by a component discriminating processor implemented by the CPU, the component discriminating step comprising discriminating components based on the respective pieces of resolution spectral data obtained by the multivariate curve resolution;

a component number determining step executed by a component number determining processor implemented by the CPU, the component number determining step comprising determining a number of the components included in the sample based on the result of discriminating the components, wherein at the multivariate curve resolution executing step, a provisional number of components is increased or decreased so that the multivariate curve resolution is repeated until a border value between a provisional number of components in a case where components are discriminated as being different in all the pieces of the resolution spectral data obtained by the multivariate curve resolution and a provisional number of components in a case where the components are discriminated as being matched in at least two pieces of the resolution spectral data in all the pieces of the resolution spectral data obtained by the multivariate curve resolution is obtained, at the component number determining step, a number of the components included in the sample is determined based on the border value, at the multivariate curve resolution executing step, when the components are discriminated as being different in all the pieces of the resolution spectral data obtained by the multivariate curve resolution, a provisional number of components is increased one by one so that the multivariate curve resolution is repeated until the components are discriminated as being matched in at least two pieces of the resolution spectral data in all the pieces of the resolution spectral data obtained by the multivariate curve resolution, at the component number determining step, when the components are discriminated as being matched in at least two pieces of the resolution spectral data in all the pieces of the resolution spectral data obtained by the multivariate curve resolution, a provisional number of components at that time is used as the border value, and a value obtained by subtracting one from the border value is determined as the number of components included in the sample, wherein at the multivariate curve resolution execution step the provisional number of components is initially set to a value of 2, and wherein in the spectral data obtainment step, the measuring device detects spectra at a plurality of measurement points on a surface of the sample, and obtains a measurement data matrix based on the spectra at each of the measurement points.

4. The automatic analysis method according to claim 3, wherein at the multivariate curve resolution executing step, when the provisional number of components reaches the predetermined repetition determined value, execution of the multivariate curve resolution is ended.

5. The automatic analysis method according to claim 3, wherein at the component discriminating step, a library of spectral data about known components is used, and all the pieces of the resolution spectral data obtained by the multivariate curve resolution is compared with the spectral data in the library, so that the components are discriminated.

6. The automatic analysis method according to claim 3, wherein at the component discriminating step, all the pieces of the resolution spectral data obtained by the multivariate curve resolution are compared with each other, and the components are discriminated based on whether similarities of the resolution spectral data are a predetermined threshold or more.

7. The automatic analysis method according to claim 3, further comprising: a concentration distribution display step executed by a display processor implemented by the CPU, the concentration distribution display step comprising displaying concentration distribution of the components discriminated at the component discriminating step as a chemical image.

8. The automatic analysis method according to claim 3, wherein in the data input step, the measurement data matrix is also input into the data input section connectable to the measuring device.

9. The automatic analysis method according to claim 8, wherein the multivariate curve resolution executing step includes calculating a spectral matrix composed of the resolution spectral data of the components based on the measurement data matrix input into the data input section.

* * * * *